US00PP17763P2

(12) United States Plant Patent
Kordes

(10) Patent No.: US PP17,763 P2
(45) Date of Patent: May 29, 2007

(54) HYBRID TEA ROSE PLANT NAMED 'KORABURG'

(50) Latin Name: *Rosa hybrida*
Varietal Denomination: KORaburg

(75) Inventor: Tim-Hermann Kordes, Offenseth-Sparrieshoop (DE)

(73) Assignee: W. Kordes' Söhne Rosenschulen GmbH & Co KG, Klein Offenseth-Sparrieshoop (DE)

( * ) Notice: Subject to any disclaimer, the term of this patent is extended or adjusted under 35 U.S.C. 154(b) by 263 days.

(21) Appl. No.: 11/071,752

(22) Filed: Mar. 2, 2005

(51) Int. Cl.
*A01H 5/00* (2006.01)

(52) U.S. Cl. ..... Plt./137

(58) Field of Classification Search ..... Plt./137, Plt./138, 148
See application file for complete search history.

(56) References Cited

PUBLICATIONS

German PBR Application ROS 2447 Apr. 5, 2004 W. Koredes' Söhne.
Q2 (CPVO) Application 20041554 Aug. 19, 2004 W. Kordes' Söhne.

*Primary Examiner*—Kent Bell
*Assistant Examiner*—June Hwu

(57) ABSTRACT

A new and distinct variety of rose with long lasting, novel warm pink flowers, and attractive foliage with good disease resistance. It exhibits uniform upright growth with abundant flowers. The new variety propagates well from traditional methods. This new and distinct variety has shown to be uniform and stable in the resulting generations from asexual propagation.

1 Drawing Sheet

CROSS REFERENCE AND FEDERAL R&D STATEMENT

There are no cross referenced or related applications. This variety was developed without the aid of any research grant.

Latin name of genus and species: The botanical classification of the new rose plant is *Rosa hybrida.*

Variety denomination: The denomination of the new variety is 'KORaburg'.

BACKGROUND OF THE INVENTION

The new variety of rose plant of the present invention originated from a controlled crossing during the summer of 1995 in a breeding program between 'TANallepa', a non-patented rose and an un-named seedling.

The resulting seeds were planted during the following winter. The resulting seedlings exhibited distinctive physical and biological characteristics. The new rose plant was selected in as a single plant from the seedling beds due to its superior characteristics and asexually propagated for further evaluation. This new and distinctive rose variety is named 'KORaburg'.

SUMMARY OF THE INVENTION

The new rose plant may be distinguished from its seed parent, TANallepa, by the following combination of characteristics:

1. Improved disease resistance,
2. a lower petal count, and
3. KORaburg flowers generally in clusters while TANallepa has single flowers.

The new rose plant may be distinguished from its pollen parent, an un-named seedling by the following combination of characteristics:

1. Larger flowers with higher petal counts, and
2. Stronger growth.

The objective of the hybridization was to create a new and distinct rose plant with unique qualities, such as:

1. Uniform growth and flowering,
2. Abundant attractive, recurrent flowers;
3. Attractive and abundant foliage, and;
3. Resistance to diseases encountered in landscapes and gardens.

This combination of qualities is not present in prior rose cultivars. These objectives have been substantially achieved and in that distinguish 'KORaburg' from all other varieties of which we are aware.

As part of the rose development program, Tim-Hermann Kordes germinated the seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORaburg' was selected in May, 1996 from the seedling beds to be asexually propagated for further evaluation. The first asexual propagation of 'KORaburg' was done by budding to seedling understocks in July, 1996 in Offenseth-Sparrieshoop, Germany.

This initial and other subsequent propagations conducted in controlled environments show that the foregoing and all other characteristics of 'KORaburg' come true to form and are transmitted through succeeding generations.

BRIEF DESCRIPTION OF THE DRAWING

The accompanying color illustration shows as true as is reasonably possible to obtain in color photographs of this type, the typical characteristics of flowers in various stages of development of KORaburg. Specifically illustrated in SHEET ONE is a cluster of flowers on a plant in the breeder's nursery.

DETAILED BOTANICAL DESCRIPTION

The following is a description of 'KORaburg', as observed in its growth in September, 2004 in a nursery in Jackson County, Oreg. on plants of 1 year of age. Color references are made using The Royal Horticultural Society (London, England) Colour Chart, 2001 except where common terms of color are used.

For a comparison, several physical characteristics of the rose variety 'Queen Elizabeth', a non-patented rose variety, are compared to 'KORaburg' in Chart 1.

CHART 1

| | 'KORaburg' | 'Queen Elizabeth' |
|---|---|---|
| General tonality | Red-Purple Group 58C. | Red Group 50C. |
| Flower size | 10–12 cm | 9–10 cm |
| Overall height | 120 cm | 130–180 cm |

Parents:

*Seed parent.*—'TANallepa'.

*Pollen parent.*—Un-named seedling.

Classification:

*Botanical classification.*—*Rosa hybrida.*

*Commercial classification.*—Hybrid Tea.

FLOWER AND FLOWER BUD

Blooming habit: Recurrent.

Flower bud:

*Size.*—Upon opening, 20–28 mm in length from base of receptacle to end of bud.

*Bud form.*—Long. Pointed ovoid to ovoid.

*Bud color.*—As sepals first unfold, bud color is Red-Purple Group 60B. When ¼ open, the upper surface of petals is Red-Purple Group 60C, and the lower surface is Red-Purple Group 60B.

*Sepals.*—Size: Average 30 mm long×13 mm wide. Shape: Strong foliaceous appendages on three of the five sepals. Sepal apex is cirrose. Base is flat at union with receptacle. Quantity: Five. Surface texture: Upper and lower surfaces with slight to moderate pubescence. Stipitate glands present on margins. Color: Upper surface Green Group 138A. The upper surfaces express intonations of Greyed-Green Group 187A. Lower surface Green Group 138A. The lower surfaces express intonations of Greyed-Green Group 179A.

*Receptacle.*—Surface: Smooth. Color: Green Group 138A. Shape: Funnel shaped. Size: 8 mm (h)×10–12 mm (w).

*Peduncle.*—Surface: With moderate numbers of stipitate glands. Length: 50–70 mm average length. Diameter: 2–3 mm average diameter. Color: Greyed-Red Group 183C. Strength: Strong. Borne: 1–4 buds per flowering stem.

Flower bloom:

*Fragrance.*—Moderate fragrance of species rose.

*Duration.*—Six days on the plant. Senesced petals drop away cleanly. As a cut flower, 3 to 4 days.

*Size.*—Medium flowered garden rose. Average flower diameter is 10–12 cm when open.

*Form.*—Shape of flower when viewed from the side: Upon opening, upper part: Flattened convex. Upon opening, lower part: Convex. Open flower, upper part: Flattened convex. Open flower, lower part: Flat.

Color:

*Upon opening, petals.*—Outermost petals: Outer Side: Marginal zone Red-Purple Group 61C. Middle of the petal Red-Purple Group 58B. Inner Side: Red-Purple Group 61B. Innermost petals: Outer Side: Marginal zone of the petal Red-Purple Group 61C. Middle zone of the petal Red-Purple Group 58B. Inner Side: Red-Purple Group N66B.

*Upon opening, basal petal spots.*—Basal petal spot, outermost petals: Outer Side: Yellow Group 1D. Inner Side: Yellow Group 1D. Basal petal spot, innermost petals: Outer Side: Yellow Group 1D. Inner Side: Yellow Group 1D.

*After opening, petals.*—Outermost petals: Outer Side: Red-Purple Group N66D. Inner Side: Red-Purple Group N66C. Innermost petals: Outer Side: Red-Purple Group N66D. Inner Side: Red-Purple Group N66C.

*After opening, basal petal spots.*—Basal petal spot, outermost petals: Outer Side: Yellow Group 1D. Inner Side: Yellow Group 1D. Basal petal spot, innermost petals: Outer Side: Yellow Group 1D. Inner Side: Yellow Group 1D. Variegations: Occasional white streak, White Group N155B on the guard petals and some inner petals.

General tonality: On open flower Red-Purple Group 58C. No change in the general tonality at the end of the $4^{th}$ day. Afterwards, general tonality is Red-Purple Group 67D.

Petals:

*Petal count.*—Approximately 25–30 petals under normal conditions.

*Petal reflex.*—Outermost petals reflex slightly.

*Petal edge.*—Entire.

*Petal shape.*—Apex shape is round. Shape of base is acute.

*Petal size.*—55–60 mm long; 50–55 mm wide.

*Thickness.*—Thick.

*Petal arrangement.*—Informal.

*Petaloids.*—Present. Average of 1–3 per flower. Petaloids are 18–25 mm long and 6–8 mm wide. Color of inner side is Red-Purple Group 58C. Color of outer side is Red-Purple Group 58C. Surface texture is smooth. Shape is linear to elliptic.

Reproductive organs:

*Pistils.*—Approximately 120 present. Stigmas: Location: Inferior in location to anthers. Color: Green-White Group 156D. Styles: Length: 15–20 mm long. Color: Red-Purple Group 67A.

*Stamens.*—Approximately 110–120 on average and regularly arranged around the styles. Anthers: Size: 1.5–2.0 mm long. Color: Greyed-Orange Group 163C. Pollen: Scant. Color: Greyed-Orange Group 177D. Filaments: Color: White Group 155C. Length: 12–15 mm.

THE PLANT

Plant growth: Moderate vigor. Upright to bushy habit. When grown as a budded nursery plant the average plant height is 120 cm and the average plant width is 80 cm.

*Stems.*—Stem color: Young wood: Green Group 138A with intonations of Greyed-Red Group 183C. Older wood: Green Group 138A with intonations of Greyed-Red Group 183C. Stem surface: Young wood: Smooth. Older wood: Smooth.

*Prickles.*—Present. Incidence: 10 per 10 cm of stem. Size: Average length: 6–7 mm. Color: Immature prickles colored Greyed-Red Group 183C to Greyed-Red Group 179C. Mature prickles colored near Greyed-Red Group 183A. Grey-Brown Group N199A at senescence. Shape: Linear to downward hooked.

*Leaves and leaflets.*—Normally 5 leaflets on normal leaves in middle of the stem. Some leaves with 1–2 smaller additional leaflets towards the base. Base of leaflet is rounded. Apex of leaflet slightly pointed. Leaf size: 160 mm (l)×120 mm (w). Quantity: Average abundance. Texture: Semi glossy on upper side. Leathery. Color, mature foliage: Upper Leaf Surface: Green Group 139A. Lower Leaf Surface: Green Group 138A. Color, juvenile foliage: Upper Leaf Surface: Green Group 139A. Lower Leaf Surface: Green Group 138A. Anthocyanin intonation: Present. Color Greyed-Red Group 183C. Location: Intonations present on upper and lower leaflet surfaces, leaf petioles, and leaf rachis of developing leaves.

*Stipules.*—Size: 12 mm (l) and 3–4 mm (w). Stipule color: Green Group 138A. Presence of stipitate glands: Abundant on margins and undersides. Margins: Bearded. Serrated.

*Petiole.*—Length: Range of 5 mm–20 mm. Diameter: 2–2.5 mm average diameter. Petiole color: Green Group 138A. Underneath: Green Group 138A. Anthocyanin: Present. Greyed-Red Group 183C. Stipitate glands: Present on margins.

*Petiole rachis.*—Color: Green Group 138A. Underneath: Green Group 138A. Anthocyanin: Present. Greyed-Red Group 183C. Stipitate glands: Present on margins.

*Leaflets.*—Size: Average terminal leaflet is 65mm (l)× 45 mm(w). Shape: Pointed oval. Margins: Serrated. Texture: Leathery.

Hips/seed formation: None observed.

Winter hardiness observation: To date, the new variety has been grown successfully in Zone 5.

Disease resistance: Above average resistance to blackspot, powdery mildew, and rust diseases under normal growing conditions.

I claim:

1. A new and distinct variety of rose plant characterized by the following combination of characteristics:

(a) Forms abundant, attractive, fragrant, and warm pink colored flowers;

(b) exhibits an upright and bushy growth habit;

(c) is suited for traditional propagation (d) exhibits flowers and foliage with excellent disease resistance;

substantially as herein illustrated and described.

* * * * *

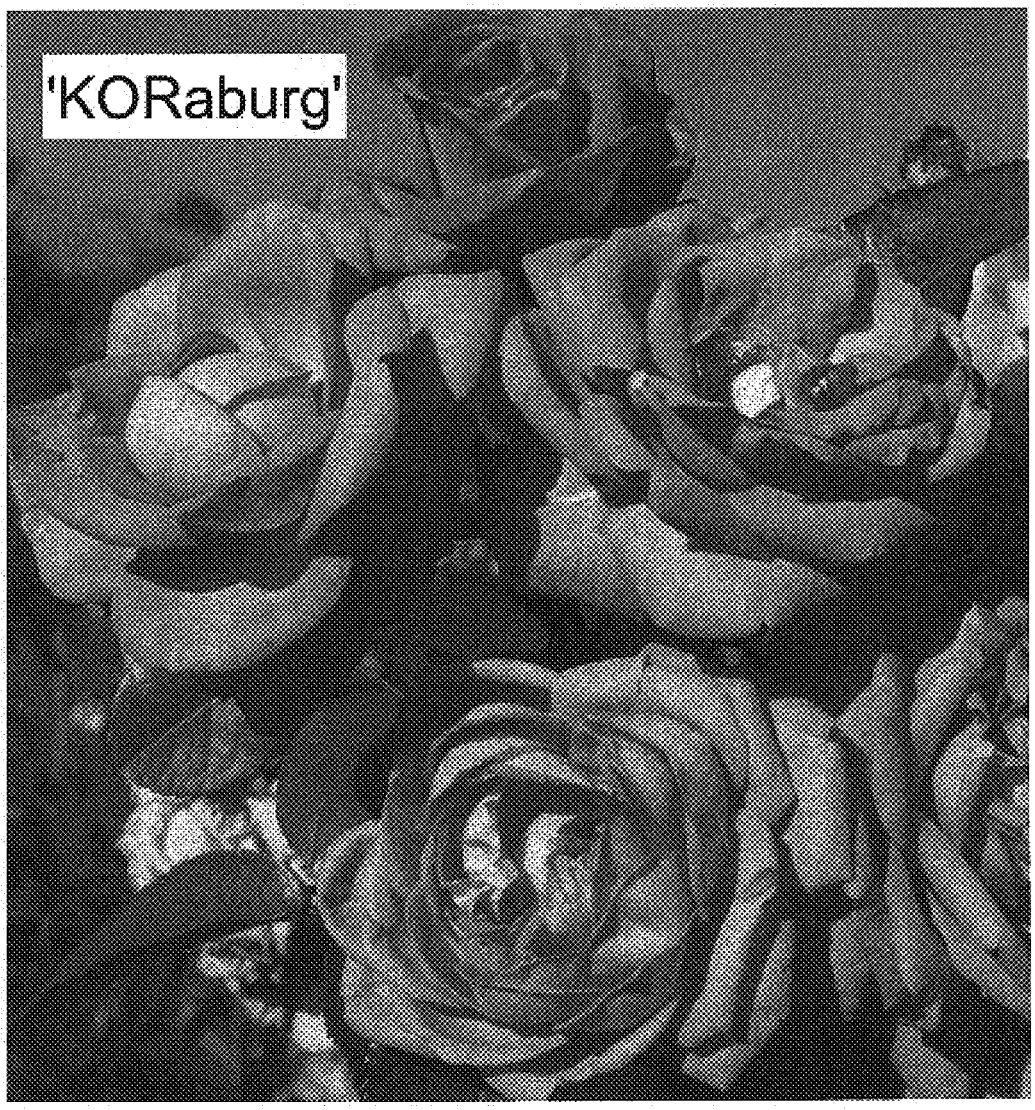
'KORaburg'